(12) United States Patent
Teoule et al.

(10) Patent No.: US 6,210,932 B1
(45) Date of Patent: Apr. 3, 2001

(54) SYSTEM FOR DETECTING NUCLEIC ACID HYBRIDIZATION, PREPARATION METHOD AND APPLICATION THEREOF

(75) Inventors: Robert Teoule, Grenoble; Sylvie Sauvaigo, Herbeys; Hervé Bazin, Villeneuve les Avignon, all of (FR)

(73) Assignee: CIS BIO International, Saclay (FR)

(*) Notice: Subject to any disclaimer, the term of this patent is extended or adjusted under 35 U.S.C. 154(b) by 0 days.

(21) Appl. No.: 09/402,764
(22) PCT Filed: Apr. 9, 1998
(86) PCT No.: PCT/FR98/00722
  § 371 Date: Dec. 3, 1999
  § 102(e) Date: Dec. 3, 1999
(87) PCT Pub. No.: WO98/45475
  PCT Pub. Date: Oct. 15, 1998

(30) Foreign Application Priority Data

Apr. 9, 1997 (FR) .................................................. 97 04328

(51) Int. Cl.[7] .............................. C12P 19/34; C12Q 1/68; C07H 21/02; C07H 21/04; G01N 33/00
(52) U.S. Cl. ............................ 435/91.1; 435/6; 435/91.2; 536/23.1; 536/24.3; 536/24.33; 436/94
(58) Field of Search .............................. 435/6, 91.1, 91.2, 435/183, 975; 436/94; 536/23.1, 24.3, 24.33, 25.3

(56) References Cited

FOREIGN PATENT DOCUMENTS

| 0 416 817 | 3/1991 | (EP) . |
| 0 501 356 | 9/1992 | (EP) . |
| WO 96 06946 | 3/1996 | (WO) . |

OTHER PUBLICATIONS

Newton et al., The production of PCR products with 5' single–stranded tails using primers that incorporate novel phosphoramidite intermediates. Nucleic Acids Res. 21, 1155–1162, 1993.*

Stratagene Catalog (1988) p. 39, Published by Stratagene, 11011 North Torrey Pines Road, La Jolla, CA 92037, 1988.*

Newton C. R. et al., "The Production of PCR Products with 5' Single–Stranded Tails Using Primers that Incorporate Novel Phosphoramidite Intermediates", *Nucleic Acid Research*, 1993, pp. 1155–1162, vol. 21, No. 5.

* cited by examiner

Primary Examiner—Bradley L. Sisson
Assistant Examiner—Frank Lu
(74) Attorney, Agent, or Firm—Alston & Bird LLP

(57) ABSTRACT

The invention concerns nucleic acid detection using a probe consisting of: a binding domain A, consisting of a single strand polynucleotide; and intermediate domain B, consisting of at least a stop synthon; and a display domain C, consisting of a double strand polynucleotide, wherein is incorporated at least a marked nucleotide constituting detection means. The use of said probes amplifies the hybridisation signal with nucleic acid target sequences.

15 Claims, 2 Drawing Sheets

…

Figure 1:
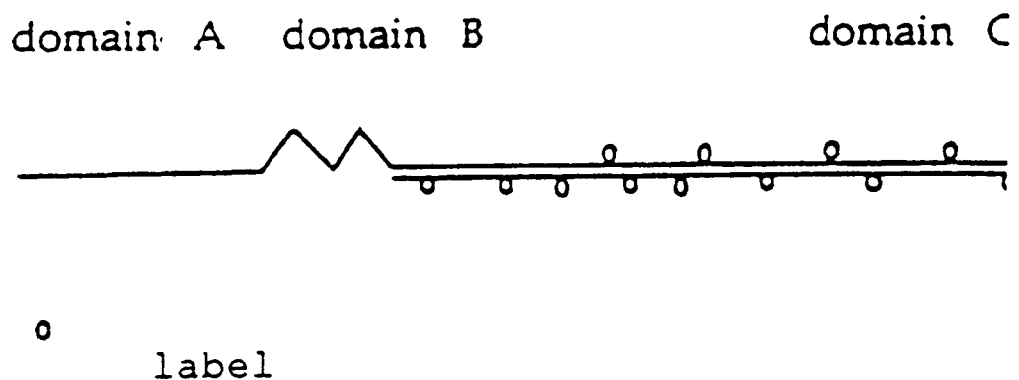

SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Nucleotide Primer
<221> NAME/KEY: misc_feature
<222> LOCATION: (16)...(16)
<223> OTHER INFORMATION: The n at position 16 is designated as "other"
      and has the following molecular structure
      -O-CH2-(CH2)4-CH2-O-PO2H-.
<221> NAME/KEY: misc_feature
<222> LOCATION: (17)...(17)
<223> OTHER INFORMATION: The n at position 17 is designated as "other"
      and has the following molecular structure:
      -O-CH2-(CH2)4-CH2-O-PO2H-.

<400> SEQUENCE: 1
accatcgctt ccaganngca aggcaggagc tgcagga                          37

<210> SEQ ID NO 2
<211> LENGTH: 20
<212> TYPE: DNA
<213> ORGANISM: Artificial Sequence
<220> FEATURE:
<223> OTHER INFORMATION: Nucleotide Primer

<400> SEQUENCE: 2
gattgcccta gagtgcagtg                                            20

<210> SEQ ID NO 3
<211> LENGTH: 37
<212> TYPE: DNA
<213> ORGANISM: Artificial Sequence
<220> FEATURE:
<223> OTHER INFORMATION: Nucleotide Primer
<221> NAME/KEY: misc_feature
<222> LOCATION: (16)...(16)
<223> OTHER INFORMATION: The n at position 16 is designated as "other"
      and has the following molecular structure:
      -O-CH2-(CH2)4-CH2-O-PO2H-.
<221> NAME/KEY: misc_feature
<222> LOCATION: (17)...(17)
<223> OTHER INFORMATION: The n at position 17 is designated as "other"
      and has the following molecular structure:
      -O-CH2-(CH2)4-CH2-O-PO2H-.

<400> SEQUENCE: 3
accatcgctt ccaganngct gaagtggtgg aaaccgc                          37

<210> SEQ ID NO 4
<211> LENGTH: 20
<212> TYPE: DNA
<213> ORGANISM: Artificial Sequence
<220> FEATURE:
<223> OTHER INFORMATION: Nucleotide Primer

<400> SEQUENCE: 4
ctgcctgcat ctcttcgacc                                            20

<210> SEQ ID NO 5
<211> LENGTH: 20
<212> TYPE: DNA
<213> ORGANISM: Artificial Sequence
<220> FEATURE:
<223> OTHER INFORMATION: Nucleotide Primer

<400> SEQUENCE: 5
cagcgacctt gtccacctcc                                                          20

<210> SEQ ID NO 6
<211> LENGTH: 43
<212> TYPE: DNA
<213> ORGANISM: Artificial Sequence
<220> FEATURE:
<223> OTHER INFORMATION: Nucleotide Primer
<221> NAME/KEY: misc_feature
<222> LOCATION: (22)...(22)
<223> OTHER INFORMATION: The n at position 22 is designated as "other"
      and has the following molecular structure:
      -O-CH2-(CH2)4-CH2-O-PO2H-.
<221> NAME/KEY: misc_feature
<222> LOCATION: (23)...(23)
<223> OTHER INFORMATION: The n at position 23 is designated as "other"
      and has the following molecular structure:
      -O-CH2-(CH2)4-CH2-O-PO2H-.

<400> SEQUENCE: 6
cacgtggcta ccatgccatt tnngctgaag tggtggaaac cgc                                 43

<210> SEQ ID NO 7
<211> LENGTH: 21
<212> TYPE: DNA
<213> ORGANISM: Artificial Sequence
<220> FEATURE:
<223> OTHER INFORMATION: Nucleotide Primer

<400> SEQUENCE: 7
gcctcgcata tcaggaagca c                                                        21

<210> SEQ ID NO 8
<211> LENGTH: 18
<212> TYPE: DNA
<213> ORGANISM: Artificial Sequence
<220> FEATURE:
<223> OTHER INFORMATION: Nucleotide Probe

<400> SEQUENCE: 8
tggcatggta gccacgtg                                                            18

<210> SEQ ID NO 9
<211> LENGTH: 30
<212> TYPE: DNA
<213> ORGANISM: Artificial Sequence
<220> FEATURE:
<223> OTHER INFORMATION: Target Nucleic Acid for Hybridization

<400> SEQUENCE: 9
uugccuggac gaccggqucc uuucuuggag                                               30

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide Probe

<400> SEQUENCE: 10
ggtcgtcctg gcaat                                                               15

<210> SEQ ID NO 11
<211> LENGTH: 15
<212> TYPE: DNA

-continued

```
<213> ORGANISM: Artificial Sequence
<220> FEATURE:
<223> OTHER INFORMATION: Nucleotide Primer

<400> SEQUENCE: 11
atccgttcta cagcc                                                    15

<210> SEQ ID NO 12
<211> LENGTH: 16
<212> TYPE: DNA
<213> ORGANISM: Artificial Sequence
<220> FEATURE:
<223> OTHER INFORMATION: Nucleotide Probe

<400> SEQUENCE: 12
ctccaagaaa ggaccc                                                   16
```

SYSTEM FOR DETECTING NUCLEIC ACID HYBRIDIZATION, PREPARATION METHOD AND APPLICATION THEREOF

FIELD OF THE INVENTION

The present invention relates to means for detecting nucleic acids by hybridization which can be used, in particular, for diagnosis.

BACKGROUND OF THE INVENTION

The techniques for identifying RNA or DNA sequences (target sequences) in a sample involve hybridizing the target sequence with a labelled probe and detecting the duplex which has been formed, after the unhybridized probe has been removed.

These techniques are commonly used, in particular, for diagnosing viral or infectious diseases, for medical or genetic research, for identifying clones, for analysing transcribed genes, etc.

Two types of probe are employed, i.e. so-called long probes (generally of a size larger than 100 bases) and short probes, whose sizes vary between 10 and 30 bases in length. The probes which are most commonly used in medical diagnosis are synthetic oligonucleotides which are coupled to a label, either by direct attachment to this label or by coupling to a ligand; in this latter case, detection is effected by way of a label which is fixed to this ligand.

Radioactive or cold labels can be used.

A large number of labelling techniques are described, for example by SAMBROOK et al., [Molecular Cloning: A Laboratory Manual, Cold Spring Harbor Laboratory Press, Cold Spring Harbor, N.Y. (1989)]. In the case of radioactive labels, these methods include, for example, labelling synthetic oligonucleotides 5' with $\gamma^{32}$P-ATP using the enzyme polynucleotide kinase, or else incorporating radioactive dCTP or dATP while labelling by nick translation.

Biotin may be mentioned, in particular, as an example of a non-radioactive label which can be incorporated chemically into synthetic oligonucleotides (Application PCT WO 89/12462); biotinylated analogues of UTP can also be incorporated into double-stranded DNAs by nick translation.

In general, biotin is detected by being bound to avidin, which is itself used as a support for attaching fluorescent molecules, enzymes or other detectable compounds.

In other non-radioactive labelling systems, haptens (dinitrophenyl group, digoxigenin) replace biotin and specific labelled antibodies are used as indicators in the system.

The sensitivity of molecular hybridization assays is an important factor which is often limiting when applying diagnostic tests in molecular biology.

The sensitivity of an assay depends directly on the labelling which is used to visualize the hybridized probe. One of the ways of improving the sensitivity of an assay is to amplify the signal by increasing the number of labels which are incorporated into the probe in order to obtain so-called "polylabelled" probes.

With this aim in mind, it has been proposed, for example, that the enzyme terminal transferase should be used, which enzyme is able to extend a single-stranded DNA chain by adding nucleotide analogues, for example biotinylated nucleotides, to its 3' end. The main drawback of this method is that the enzyme adds an arbitrary number of nucleotides to the end of the single-stranded DNA chain. This results in a mixture of products of different lengths which in turn makes the labelling difficult to reproduce and produces heterogeneous probes which are difficult to standardize and therefore unsuitable for medical diagnosis.

COLLINS (Application EP 204 510) proposes a variant in which the enzyme terminal transferase is used to extend the probe by adding a homopolymeric (poly A) tail to it. The label then consists of a homopolymer (poly T) into which detectable molecules are incorporated. However, this system does not completely eliminate the drawbacks which result from the impossibility of controlling the action of the enzyme.

It has also been proposed to amplify the signal by using polylabelled oligonucleotide probes which are branched or else connected to each other by polynucleotide "bridges" which hybridize to their ends, as described in Applications EP 292 128 and EP 450 594, respectively, which are in the name of SEGEV.

U.S. Pat. No. 4,882,269 describes a system in which polylabelled secondary probes hybridize to several sites on a primary probe.

Application EP 0 317 077 and also Application PCT WO 92/02526 describe a system in which the secondary probes consist of polylabelled polynucleotide constructs in comb form.

These systems suffer from the drawback of requiring the synthesis of a large number of different oligonucleotides and the implementation of hybridization and/or ligation steps in order to form the final constructs. In addition, it is difficult to obtain final products having uniform characteristics and it is awkward to purify these products.

In particular, if there is a need to detect several different target sequences, it is then necessary, for each of these sequences, either to synthesize a new probe or to use an adapter, which is an oligonucleotide which hybridizes with the target sequence to be detected, on the one hand, and with the probe, on the other hand.

SUMMARY OF THE INVENTION

The object of the present invention is to propose a system for amplifying a hybridization signal, which system does not suffer from the abovementioned drawbacks and is simple to obtain, to purify and to use, in particular when simultaneously detecting several nucleic acid sequences.

With this aim in mind, the inventors had the idea of using nucleic acid molecules of a specific structure as labelled detection probes, which molecules had only previously been used as amplification products of a target sequence which were intended to be attached to a solid support and then detected by means of standard methods, for example using a probe.

Such nucleic acid molecules are described by NEWTON et al. [Nucleic Acids Res., 21, pp. 1155–1162, (1993)], as well as in Application EP 416 817, in the name of IMPERIAL CHEMICAL INDUSTRIES PLC. They are present in the form of a double-stranded domain (which is a copy of the target sequence) which domain is provided, at at least one of its ends, with a single-stranded tail which enables the molecule to be attached to a solid support or to be visualized using a labelled probe which is complementary to the said tail. The double-stranded domain is separated from the single-stranded tail by a region which comprises a stop synthon.

These nucleic acid molecules are obtained by the polymerase chain amplification (PCR amplification) of the target sequence using primers which comprise a nucleotide sequence which is able to hybridize with the said target sequence and a polynucleotide tail, with the nucleotide sequence and the polynucleotide tail being separated by a stop synthon.

A "synthon" is a molecule (nucleotide analogue or other molecule) which is able to be incorporated into a synthetic polynucleotide. A "stop synthon" is a synthon which additionally possesses the property of causing the polymerase to stop when the latter encounters a synthon on the template strand during a reaction for copying or elongating a polynucleotide.

When a primer which contains a stop synthon is used for amplifying a target sequence in a polymerase chain amplification reaction, the polynucleotide tail which is located beyond the stop synthon is not copied and the final amplification product is therefore present in the form of a double-stranded copy of the target sequence, which copy is provided with a single-stranded tail.

The present invention relates to the use of nucleic acid molecules possessing the structure: single-stranded region/stop synthon/double-stranded region, as described above, as probes for detecting a target sequence. More precisely, the present invention relates to a process for detecting at least one target nucleic acid sequence, characterized in that the said target sequence is brought into contact with at least one detection probe which consists of a nucleic acid molecule which consists of:

- an attachment domain A, which consists of a single-stranded polynucleotide;
- an intermediate domain B, which consists of at least one stop synthon; and
- a visualization domain C, which consists of a double-stranded polynucleotide into which at least one labelled nucleotide, constituting a means of detection, is incorporated, under conditions which enable the A domain of the said nucleic acid probe to hybridize with the target sequence, and in that the hybrid which is formed is detected by way of the C domain of the said nucleic acid probe.

A detection probe which can be used for implementing the process in accordance with the invention is shown diagrammatically in FIG. 1.

The size of the attachment domain A of the detection probe is advantageously between 8 and 40 nucleotides in length, preferably from 15 to 25 nucleotides in length.

The B domain can consist of one or more identical or different stop synthons; synthons which can be used as stop synthons are, for example, selected from alkanediols, or any other compound such as those described, for example, by WILK et al. [Nucleic Acids Res., 18, pp. 2065–2068, (1990)], or by KUBAREVA et al. [Nucleic Acids Res., 20, pp. 4533–4538, (1992)], or else in the NEWTON et al. publication and in Application EP 416 817, as mentioned above.

The detection means which are incorporated into the C domain constitute an amplification signal which enables the detection probe to be visualized. In a general way, detection means which can be used within the context of the present invention are the labels which are known per se and which are conventionally employed for labelling nucleic acid probes so that the latter can be visualized. The detection means are, in particular, nucleotides or nucleotide analogues which can be incorporated by a polymerase into an oligonucleotide chain and which can be labelled so as to be detected either directly, for example in the case of radioactive labelling or in the case of labelling with a fluorescent molecule, or indirectly, for example in the case of ligands (such as biotin or a hapten), which are revealed by the attachment of labelled molecules (such as avidin or an antibody). The detection means can also be introduced into the polynucleotide chain in the form of label precursors which are intended to be modified subsequently in order to produce the molecule which emits the visualization signal.

Advantageously, at least $1/50$, preferably at least $1/10$, and very preferably at least $1/5$, of the monomers which constitute the double-stranded C domain of the detection probe are labelled nucleotides or nucleotide analogues such as defined above. These labelled monomers may be incorporated into only one of the strands of the C domain; in order to obtain more substantial labelling and a stronger signal, preference will generally be given to incorporating the labelled monomers into each of the two strands.

The level of the signal generated by the detection probe also depends on the size of the double-stranded C domain; advantageously, this size is between 0.1 and 50 kb, preferably between 1 and 10 kb.

On the other hand, the sequence of the double-stranded C domain is not of essential importance inasmuch as the only function of this polynucleotide is to enable the detection probe to be visualized as a result of the labelled nucleotides which are incorporated into this polynucleotide.

For implementing the process in accordance with the invention, the A domain of the detection probe can be hybridized directly with the target sequence; in this case, the A domain is selected such that its sequence is complementary to the target sequence to be detected. Use can also be made, if desired, of an adapter; however, in most cases, this will not be necessary even if it is desired to detect several target sequences. This is because, as will be seen below, it is very easy to prepare simultaneously detection probes which differ from each other in the sequence of the A domain.

The process in accordance with the invention is therefore particularly suitable for simultaneously detecting several target sequences.

As pointed out above, it is possible simultaneously to use several detection probes which differ from each other in the sequence of the A domain; where appropriate, these probes may also differ from each other in the nature of the B domain (that is to say the number and/or the nature of the stop synthons). Furthermore, they may differ from each other in the sequence of the C domain and/or, advantageously, in the nature of the labelling of the nucleotides which are incorporated into the said domain. This makes it possible, for example, to allocate a specific visualization signal to each target sequence.

The target sequence(s) to be detected may be attached to a solid support. Advantageously, this solid support consists of a multiplicity of electrodes, for example microelectrodes which are arranged in a matrix, at least 2 of which electrodes each carry a different target sequence. The target sequence(s) is/are, for example, attached to these electrodes using the methods which are described in Application PCT WO/94/22889.

Detection probes which can be used in accordance with the invention for detecting a target sequence can easily be obtained by enzyme synthesis, by using a polymerase to extend at least one primer, which contains at least one stop synthon, in an appropriate reaction mixture which comprises at least one nucleotide or one labelled nucleotide analogue.

The present invention also relates to detection probes which can be used in accordance with the invention for detecting a target sequence, and to the process for preparing them.

A process for preparing detection probes in accordance with the invention comprises at least one step during which at least one of the strands of the C domain is synthesized by elongating, using a polymerase, in the presence of a template strand and in an appropriate reaction mixture, a primer P', which comprises, from 5' to 3': an A domain and a B domain as defined above and an X domain which consists of a sequence which is able to hybridize with the template strand in order to prime the polymerization, and is characterized in that all or part of at least one of the nucleotide triphosphates of the reaction mixture is replaced with one of its labelled derivatives.

Figure 2:
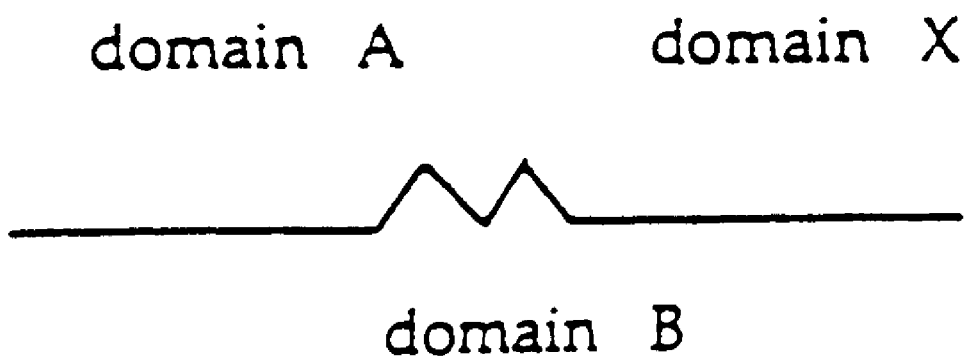

The structure of the primer P' is shown diagrammatically in FIG. 2.

Under these conditions, the polymerase incorporates the labelled nucleotide derivatives into the newly synthesized primer elongation product in place of all or part of the corresponding nucleotides.

It is possible in this way to label the C domain to a substantial extent. For example, if, in the theoretical case of a fragment of 10 kb in size (that is 20,000 nucleotides if the fragment is double-stranded), ⅓ of the thymidine triphosphates are replaced with a labelled analogue, and assuming that a sequence to be amplified is one in which the 4 bases are present in equal proportions, a fragment is then obtained in which more than 800 labelled monomers have been incorporated/strand.

According to one preferred embodiment of the process in accordance with the invention, the polymerase elongation takes place in the presence of a second primer P'' which comprises a sequence which is able to hybridize with the elongation product of the P' primer.

The primer P'' is elongated until the polymerase encounters a stop synthon which is present in the elongation product of primer P'; the elongation product of primer P'' can hybridize to the X domain of a P' primer and be used as the template for the following elongation step. The reaction can be continued, and these steps can be repeated, in accordance with the conventional scheme of polymerase chain amplification methods until the desired quantity of detection probes in accordance with the invention has been obtained.

For this purpose, the process in accordance with the invention can be carried out under the normal conditions of the known methods of polymerase chain amplification (PCR). It is possible, for example, to use a polymerase chain amplification method which is of the same type as those described in the NEWTON et al. publication or in Application EP 416 817, as mentioned above; while being similar in their overall structure (single-stranded region/stop synthon/double-stranded region) to the nucleic acid molecules which are obtained by these methods, the detection probes in accordance with the invention differ from these latter molecules in the presence of labelled oligonucleotides in the double-stranded portion which results from the amplification.

For obtaining detection probes in accordance with the invention, the template which is used for obtaining the double-stranded C domain can be of any sequence whatsoever, termed a "neutral sequence" below, due to the fact that it is, in particular, completely independent of the target sequences which are intended to be detected using these probes. In order to improve the yield of the reaction, in particular when a polymerase chain amplification reaction is being carried out, preference is given to selecting a sequence which is rich in A and T bases, since this type of sequence generally amplifies more efficiently than do sequences which are rich in G and C.

The 5' A domain of primer P' should be selected such that it does not interfere in the elongation of the neutral sequence; in particular, it should not hybridize stably with this sequence (this can easily be verified in advance using software for analysing sequence homology). This domain should not exhibit any sequence complementarity, either with the X domain of the same P' primer or with any region of the P'' primer.

The position of the P'' primer and the X part of the P' primer on their respective templates determines the size of the C domain. This size can be very substantial. Thus, various techniques known to the skilled person make it possible to obtain elongation fragments of several tens of kilobases in length easily and with good yields [BARNES, Proc. Natl. Acad. Sci. USA 91, pp. 2216–2220 (1994); CHENG et al., Proc. Natl. Acad. Sci. USA, 91, pp. 5695–5699 (1994)].

The P'' primer at least comprises the sequence which is able to hybridize with the said template strand in order to prime the polymerization; however, it can additionally comprise an A domain and a B domain as defined above and can therefore have the same structure as the P' primer. In this case, the A and B domains of the P' and P'' primers can be identical or different.

Within the context of carrying out the process for preparing detection probes in accordance with the invention, problems associated with the fidelity of the DNA polymerases do not arise insofar as the degree of homology between the C domain and the "neutral sequence" employed as the initial template is of no importance and it is only the length of the C domain and the number of labels which can be incorporated into it which matter.

According to a preferred embodiment of the process for preparing detection probes according to the invention, use is made, in one and the same reaction mixture, of a series of P' primers which are identical to each other as regards the sequence of the X domain which hybridizes with the neutral sequence and which differ from each other in the sequence of the A domain and, where appropriate, in the nature of the B domain. This makes it possible simultaneously to prepare probes for detecting several different target sequences. If it is desired to prepare simultaneously probes which also differ from each other at the level of the C domain, the reaction mixture can contain several "neutral sequences" and the appropriate P' primer and P" primer series for each of these sequences.

The present invention also relates to a kit for preparing detection probes in accordance with the invention, characterized in that it comprises at least one P' primer as defined above, a polynucleotide which can be used as a template for elongating the said primer, and a labelled nucleotide triphosphate. Advantageously, the said kit additionally comprises a P" primer.

A large number of purification methods, which are known per se, can be used for purifying the detection probes according to the invention at the conclusion of the enzyme reaction used for obtaining them. These methods remove the unincorporated primers and nucleotide triphosphates and the residual enzyme. The sought-after fragments are recovered in good yields. These methods can be applied either directly to the product of the enzyme reaction or else after it has been isolated following migration on an electrophoresis gel.

The quality of the amplification products obtained can easily be checked by agarose gel electrophoresis. If the amplification conditions selected are good, only one band is seen on the gel. The purified product can be quantified by UV spectrometry or else by assaying the incorporated label.

Making use of the process in accordance with the invention results, in a simple and reproducible manner, in labelled detection probes which possess uniform characteristics, which are easy to quantify and purify using conventional methods and which have a very high specific activity, which activity is greater than that of the labelled probes which are normally obtained by nick translation.

Furthermore, the detection probes according to the invention exhibit the following advantages:

They possess a hybridization kinetics which is very rapid and is about the same as the hybridization kinetics of the oligonucleotides; as in the case of the oligonucleotides, this kinetics is linked, above all, to their concentration in the medium and in relation to the target sequence; this enables the hybridization and washing conditions which are required for the hybridization specificity of the detection probes according to the invention to be readily defined.

Since the recognition domain C is in double-stranded form, there is no risk of any cross hybridization of this domain with the target sequence and therefore there is no problem of any background noise.

The molecules which are incorporated into this recognition domain and which are used for visualization are sufficiently spaced out for there not to be any steric hindrance which might possibly interfere with their binding to a ligand.

The present invention will be more fully understood with the aid of the remainder of the description which follows and which refers to examples of obtaining and using detection probes according to the invention.

It should, however, be understood that these examples are given solely by way of illustrating the subject-matter of the invention, to which they in no way constitute a limitation.

PREFERRED EMBODIMENTS OF THE INVENTION

Example 1

Amplification of Different Nucleic Acid Sequences Using Primers Which Contain a Stop Synthon A) Amplification of a 1010 base pair fragment of human DNA.

P' primer:

$J_{15}(stop)_2 H_{12170}$:

5' ACC ATC GCT TCC AGA (stop)$_2$ GCA AGG CAG GAG CTG CAG GA 3' (SEQ ID NO:1)

The B domain of this primer contains 2 consecutive stop synthons, with each of these synthons consisting of a 6-hexyl phosphate unit of the following structure:

—O—CH$_2$—(CH$_2$)$_4$—CH$_2$—O—PO$_2$H—

P" primer:

$H_{13180}$:

5' GAT TGC CCT AGA GTG CAG TG 3 '(SEQ ID NO:2)

The amplification conditions were first of all finalized using unmodified primers, that is primers which did not contain the A and B domains. The amplification was then repeated using the modified P' primer containing the three A, B and C domains.

The amplification is carried out on 0.1 µg of human genomic DNA (CLONTECH) in the presence of 10 pmol of each of the primers, 2.5 units of Taq polymerase (CIS BIO INTERNATIONAL), 5 µl of 10×buffer (100 mM Tris/HCl, pH 9; 500 mM KCl; 15 mM MgCl$_2$; 1% Triton X100; 2 mg of BSA/ml, CIS BIO INTERNATIONAL) and 0.75 µl of each of the nucleotide triphosphates (20 mM solutions, BOEHRINGER MANNHEIM). After a first denaturation at 94° C. for 5 minutes, 35 cycles of the following sequences are carried out: 94° C. for 1 min. 30", 60° C. for 1 min. 30", 70° C. for 1 min. 30", and a final elongation at 70° C. for 5 min. The result is visualized after migration on a (2%/1%) NUSIEVE®/AGAROSE gel.

A single band of the expected length is obtained.

The yield and the specificity of the reaction using the modified primer and using the unmodified primer are equivalent.

B) Amplification of 6023 base pair and 10709 base pair fragments of phage λ DNA.

P' primer:

$J_{15}(stop)_2 \lambda_1$:

5' ACC ATC GCT TCC AGA (stop)$_2$ GCT GAA GTG GTG GAA ACC GC 3' (SEQ ID NO:3)

The B domain of this primer contains 2 consecutive stop synthons which are identical to those described in A) above.

P" primer:

$\lambda_{6528}$:

5' CTG CCT GCA TCT CTT CGA CC 3' (SEQ ID NO:4)

or else $\lambda_{11215}$:

5' CAG CGA CCT TGT CCA CCT CC 3'   (SEQ ID NO:5)

The primer $J_{15}(stop)_2\lambda_1$ amplifies a 6023 bp fragment when it is used with the $\lambda_{6528}$ primer and a 10709 bp fragment when it is used with the $\lambda_{11214}$ primer.

The XL PCR (PERKIN ELMER) kit is used in accordance with the protocol recommended by the manufacturer, as is the hot-start technique.

The lower phase of the reaction medium is prepared in thin-walled 500 µl tubes (PERKIN-ELMER) in accordance with the manufacturer's instructions. 40 pmol of primers are used, as is a final $Mg(OAc)_2$ concentration of 1.1 mM. The lower phase is covered with wax (PERKIN-ELMER); the upper phase is then added. The amplification is carried out on 1 ng of phage λ DNA.

The amplification takes place in accordance with the following protocol:

94° C. for 1 minute;
10 cycles of: 94° C. for 15 sec./68° C. for 5 minutes;
20 cycles of: 94° C. for 15 sec./68° C. for 5 minutes, with an increment of 15 seconds per cycle;
a final elongation at 72° C. for 10 minutes.

The amplification products are checked after electrophoresis on a 0.8% agarose gel and staining with ethidium bromide. Only one band of the expected length is seen.

C) Amplification of a 20874 base pair fragment of phage λ DNA.

P' primer:
$K_{20}(stop)_2\lambda_1$:

5' CAC GTG GCT ACC ATG CCA TTT(stop)$_2$ GCT GAA GTG GTG GAA ACC GC   (SEQ ID NO:6)

The B domain of this primer contains 2 consecutive stop synthons which are identical to those described in A) above.

P'' primer:

5' GCC TCG CAT ATC AGG AAG CAC   (SEQ ID NO:7)

The amplification is carried out on 1 ng of phage λ DNA using the primers $\lambda_2$ and $K_{20}(stop)_2\lambda_1$. The reagents are the same as in B above. The amplification conditions are as follows:

94° C. for 1 min.;
18 cycles of 94° C. for 1 min./68° C. for 10 min.;
15 cycles of 94° C. for 1 min./68° C. for 10 min., with an increment of 15 sec per cycle;
72° C. for 10 min.

The amplification is checked after electrophoresis on a 0.6% agarose gel.

One single band of the expected size is seen.

The oligonucleotide which is complementary to the A domain of the $K_{20}(stop)_2\lambda_1$ primer is used for verifying that the A domain is indeed in single-stranded form following amplification; this complementary oligonucleotide has the sequence:

5' TGG CAT GGT AGC CAC GTG 3'   (SEQ ID NO:8)

and is labelled 5' using polynucleotide kinase in the presence of $\gamma^{32}$P-ATP. It is hybridized in solution, at 37° C. for 10 minutes, with 5 µl of the amplification product in a 1×PBS, 0.25M NaCl buffer. The hybridization product is separated by electrophoresis on a 0.6% agarose gel. The gel is dried and then autoradiographed overnight. The autoradiograph shows that the radioactivity is located at the top of the gel in the area of the amplification band as well as the bottom of the gel in the area of the unhybridized labelled oligonucleotide.

The presence of the radioactivity in the area of the 20.8 kb band shows that the labelled oligonucleotide has indeed hybridized onto a single-stranded complementary fragment.

These examples demonstrate that it is easily possible to obtain very long fragments (up to 20,000 bp) using primers of the P' type and that the single-stranded part remains in this form after the amplification reaction.

Example 2

Detection of a Target Nucleic Acid; Demonstration of Signal Amplification with a Detection Probe in Accordance with the Invention Target The target is an RNA of 30 bases in length which is obtained by in-vitro transcription and whose sequence is as follows:

5' UUG CCU GGA CGA CCG GGU CCU UUC U(SEQ ID NO:9)

Solutions are prepared which are diluted 10-fold at each step. The undiluted solution is regarded as being solution 1.

Method

The target is detected by sandwich hybridization using a capture probe, which is attached to a microsupport, and an oligonucleotide (G4), which oligonucleotide is either labelled with biotin, and thereby constituting a detection probe of the conventional type, which probe is used for comparison, or detected using a detection probe in accordance with the invention.

The oligonucleotide G4, whose sequence is as follows:

5' GGT CGT CCT GGC AAT 3',   (SEQ ID NO: 10)

is labelled either with a biotin at its 5' end using the method described in Application PCT WO/89/12462, or else provided with an additional sequence (sequence $I_{15}$) at its 3' end.

The sequence $I_{15}$:

5' ATC CGT TCT ACA GCC 3'   (SEQ ID NO:11)

hybridizes specifically with an oligonucleotide ($cI_{15}$–$cJ_{15}$) one part of which is complementary to $I_{15}$ and one part of which is complementary to the sequence $J_{15}$. The whole structure G4 $I_{15}$+$cI_{15}cJ_{15}$ plays the role of an adapter.

Preparation of a Hybridization Detection Probe in Accordance with the Invention

The detection probe in accordance with the invention is obtained by PCR amplification of a human DNA fragment using the primers $J_{15}(stop)_2H_{12170}$ and $H_{13180}$ (see Example 1A). The reaction medium contains 0.1 µg of human DNA in 1×Taq buffer (CIS BIO INTERNATIONAL) together with 2.5 U of Taq DNA polymerase (CIS BIO INTERNATIONAL) and 6 pmol of each of the primers. The concentrations of the nucleotide triphosphates are 300 nM, apart from that of dTTP, which is 240 nM. The amplification medium additionally contains 60 nmol of of bio-16-dUTP (BOEHRINGER-MANNHEIM, France). The amplification conditions are as follows: 94° C. for 5 min., then 35 cycles of 94° C. for 1 min., 60° C. for 1 min. 30 sec. and 70° C. for 1 min. 30 sec., and a final elongation at 70° C. for 5 min. This results in a 1010 base pair double-stranded fragment in which approximately ⅕th of the thymidines are replaced with biotinylated uridines.

The amplification is checked on a 1% agarose gel. A single band of expected size is obtained. The fragment is purified on a SEPHACRYL® HR (MICROSPIN™ S400, PHARMACIA) column.

Hybridization on a Chip

The chip contains 48 square electrodes having a side length of 50 μm. The capture probe Gc, which has the following sequence:

5' CTC CAA GAA AGG ACC C 3',    (SEQ ID NO:12)

and 2 oligonucleotides of differing sequence (T1 and T2), which are used as controls, are each attached to an electrode by their 5' end by means of copolymerizing with pyrrole in accordance with the method described in Application PCT WO94/22889.

The hybridizations take place at 45° C. for 1 hour in a 1×PBS, 0.5M NaCl, 10 mM EDTA, 2.5×DENHARDT buffer containing 100 μg of sonicated herring sperm DNA/ml. The hybridization solutions are heated at 80° C. for 3 min. in microtubes in the presence of the RNA to be assayed and then transferred into a hybridization sac in which the chip is placed.

Detection with the Biotinylated G4 Oligonucleotide

The target RNA is hybridized onto the chip in 20 μl of 1×buffer containing 1 μl of the RNA solution to be tested and 15 pmol of the biotin-labelled G4 oligonucleotide. 3 rinses in a 1×PBS buffer containing 0.5M NaCl and 0.05% Tween 20 are then carried out. The chip is then incubated for 10 minutes in a 5 ng/μl solution of streptavidin-phycoerythrin in PBS/NaCl/Tween, after which it is rinsed in the washing buffer.

The chip is mounted on a slide, and under a cover slip, in a drop of PBS/NaCl/Tween buffer. The signal is recorded, after irradiating at 500–550 nm for 1 second, by a microscope which is coupled to a CCD camera.

Detection with the Detection Probe in Accordance with the Invention

This takes place in 2 steps.

a) Hybridization using the adapter:

The RNA to be tested (1 μl) is first of all hybridized onto the chip using 25 pmol of the $I_{15}G_4$ oligonucleotide and 25 pmol of the $cI_{15}cJ_{15}$ oligonucleotide. The chip is treated for 2×5 minutes in a 0.1N NaOH solution and rinsed with distilled water.

b) Hybridization using the detection probe:

After having been rapidly rinsed in the PBS/NaCl/Tween buffer, the chip is transferred into a second hydridization sac, which contains 10 μl of the purified detection probe in accordance with the invention and 10 μl of 2×hybridization buffer. The rinsings, the visualization with streptavidin-phycoerythrin and the recording of the signal are carried out as described above.

The signals are recorded after an irradiation of 1 second.

Results

The signal on each electrode is quantified in arbitrary fluorescence units (AFUs); the signal range is linear from 0 to 250 AFUs. The results (expressed in AFUs) obtained for the electrodes carrying the capture probe Gc are shown in Table I below.

TABLE I

| RNA dilution/Labelling | 1 | 1/10 | 1/100 | 0 (control without RNA) |
|---|---|---|---|---|
| Biotinylated G4 | 80 | 37 | 18 | 10 |
| Detection probe in accordance with the invention | 250 | 250 | 220 | 10 |

The control electrodes, carrying the T1 and T2 oligonucleotides, give signals of between 4 and 10 AFUs (results not shown in the table), which corresponds to the background noise. Under the conditions employed, a signal of 250 AFUs corresponds to the reading system being saturated.

It can be seen that the signal which is obtained with the G4 oligonucleotide labelled with a single biotin decreases very rapidly as the dilution increases, whereas using a detection probe in accordance with the invention results in a stronger signal being obtained and, in addition, markedly increases the sensitivity of the test. The background noise is the same either in the presence of the detection probe in accordance with the invention or in the presence of the conventional probe consisting of the biotinylated G4 oligonucleotide.

Example 3

Use of a Detection Probe in Accordance with the Invention for Visualization of a Microplate A detection probe which is in accordance with the invention and which is labelled with digoxigenin is prepared using the protocol described in Example 1A) above while replacing ⅕th of the dTTPs with digoxigenin-11-2'-deoxyuridine-5'-triphosphate (BOEHRINGER-MANNHEIM).

The tests are carried out using this probe, on the one hand, and, by way of comparison, using the oligonucleotide G4 DIG (G4 oligonucleotide labelled with digoxigenin at its 5' end and purified by HPLC).

The target consists of RNA as in the previous example. 10-fold stepwise dilutions of the target are prepared. This target is attached to a streptavidin-coated microplate (LABSYSTEM) by way of the biotin-labelled Gc capture probe.

Hybridization with G4 DIG

The target RNA is incubated in 50 μl of PBS/NaCl buffer containing 30 pmol of G4 DIG and 40 pmol of biotinylated Gc capture probe. The solutions are heated at 80° C. for 3 minutes and then transferred into the wells. The plates are incubated at 42° C. for 1 hour. After 3 washings with the PBS/NaCl/Tween buffer, the plates are incubated at 37° C. for 1 hour with the peroxidase-labelled anti-DIG antibody (BOEHRINGER-MANNHEIM 75 U/ml stock solution diluted to ½₀₀₀ in PBS/NaCl containing 3% BSA).

Hybridization Using the Detection Probe in Accordance with the Invention

This takes place in 2 steps:

a) Hybridization using the adapter:

The RNA to be tested is first of all hybridized in 50 μl of PBS/NaCl/Tween buffer containing 40 pmol of Gc-biotin probe, 40 pmol of $I_{15}G4$ and 40 pmol of $cI_{15}cJ_{15}$. The solutions are denatured at 80° C. for 3 minutes and then transferred into the wells of the microplate. The incubation takes place at 42° C. for 1 hour. 3 washings with PBS/NaCl/Tween are performed, with the next step being incubation with the detection probe.

b) Hybridization using the detection probe:

50 μl of PBS/NaCl containing 5 μl of the purified solution of the digoxigenin-labelled detection probe and 3% BSA are added to each well. The microplates are incubated at 42° C. for 1 hour. After 3 washings, the plates are incubated, at 37° C. for 1 hour, with the 1/4000-diluted anti-DIG antibody.

Visualization

After 3 washings, the wells are incubated in the dark in the presence of 50 μl of peroxidase substrate (O-phenylenediamine in a citrate-phosphate buffer, pH 5.5, containing 0.02% $H_2O$). The reaction is stopped, after 10 minutes in the case of the amplification system and after 30 minutes in the case of the controls, with 50 μl of 1M oxalic acid. The optical density is read at 492 nm.

The results, expressed in optical density units, are compiled in Table 11 below.

TABLE II

| RNA dilution | 1 | 1 | $10^{-1}$ | $10^{-2}$ | $10^{-3}$ | $10^{-4}$ | $10^{-5}$ | $10^{-6}$ | 0 |
|---|---|---|---|---|---|---|---|---|---|
| ml | 5 | 1 | 1 | 1 | 1 | 1 | 1 | 1 | 0 |
| Control (G4 DIG) | 0.21 | 0.09 | 0.06 | 0.06 | 0.06 | 0.06 | 0.05 | 0.06 | 0.05 |
| Detection probe in accordance with the invention | NT | 1.59 | 1.71 | 1.74 | 0.87 | 0.44 | 0.38 | 0.40 | 0.41 |

NT: not tested

As in the previous example, a very marked increase in the signal and a very marked increase in the sensitivity of the test are observed, after subtracting the background noise, when a detection probe in accordance with the invention is used.

What is claimed is:

1. A process for detecting at least one target nucleic acid sequence, comprising contacting said target sequence with at least one detection probe which consists of a nucleic acid molecule which consists of:
   an attachment domain A, which consists of a single-stranded polynucleotide;
   an intermediate domain B, which consists of at least one stop synthon; and
   a visualization domain C, which consists of a completely double-stranded polynucleotide having a size of from about 0.1 to about 50 kb and comprising at least 1/50 of labeled nucleotides based on the total nucleotides of said double-stranded polynucleotide,
   under conditions which enable the A domain of said detection probe to hybridize with the target sequence to form a hybrid, whereby the is detected by way of the C domain of the detection probe.

2. Process according to claim 1, wherein several detection probes which differ from each other in the sequence of the A domain are used simultaneously for simultaneously detecting several target sequences.

3. Process according to claim 2, wherein the said detection probes also differ from each other in the sequence of the C domain and/or in the nature of the labelled nucleotides which are incorporated into the said domain.

4. Process according to claim 1 wherein the target sequence is attached to a solid support.

5. Process according to claim 4, wherein the said solid support consists of a multiplicity of electrodes at least 2 of which each carry a different target sequence.

6. Process for preparing a detection probe according to claim 1, which comprises at least one step during which at least one of the strands of the C domain is synthesized by elongating, using a polymerase, in the presence of a template strand and in an appropriate reaction mixture, a P' primer, which comprises, from 5' to 3': an A domain and a B domain as defined above and an X domain which consists of a sequence which is able to hybridize with the template strand in order to prime the polymerization, and wherein all or part of at least one of the nucleotide triphosphates of the reaction mixture is replaced with one of its labeled derivatives.

7. Process according to claim 6, wherein the polymerase elongation takes place in the presence of a second primer P" which comprises a sequence which is able to hybridize with the elongation product of the P' primer.

8. Process according to claim 6, wherein the reaction mixture comprises several P' primers which differ from each other in the sequence of the A domain and which are identical to each other as regards the sequence of the X domain.

9. A hybridization probe for detecting a target nucleic acid molecule, comprising:
   a singe-stranded polynucleotide covalently linked to a completely double-stranded polynucleotide by one or more stop synthons,
   wherein said single-stranded polynucleotide is capable of hybridizing to said target nucleic acid molecule, and
   wherein said double-stranded polynucleotide has a size of from about 0.1 kb to about 50 kb and comprises incorporated therein at least 1/50 of labeled nucleotides based on the total number of nucleotides in the double-stranded polynucleotide.

10. The hybridization probe of claim 9, wherein the single-stranded polynucleotide has a length of 8 and 40 nucleotides.

11. A kit for detecting a target nucleic acid molecule, comprising the hybridization probe of claim 9.

12. A kit for preparing a detection probe for detecting a target nucleic acid molecule, said probe having an attachment domain A covalently linked to a visualization domain C by an intermediate domain B, wherein said domain A consists of a single polynucleotide capable of hybridizing to said target nucleic acid molecule, said domain B consists of at least one stop synthon, and said domain C consists of a completely double-stranded polynucleotide having a size of from about 0.1 to about 50 kb and comprising at least 1/50 of labeled nucleotides of said double-stranded polynucleotide, said kit comprising a carrier being compartmentalized to receive, in one or more container means:
   a nucleotide fragment comprising a nucleotide sequence identical to the sequence of said completely double-stranded polynucleotide of said domain C;
   an oligonucleotide comprising said domain A covalently linked to the 5' end of a first nucleotide primer by said domain B, said first nucleotide primer consisting of a sequence identical to the 5' end-portion of said one strand of said double-stranded polynucleotide of said domain C;

a second nucleotide primer consisting of a sequence identical to the 5' end portion of the other strand of said double-stranded polynucleotide of said domain C, so that when used together as PCR primers in a PCR reaction using said nucleotide fragment as template in the presence of labeled nucleotides, said oligonucleotide and said second nucleotide primer lead to the formation of said detection probe; and directions for using the kit to prepare said detection probe.

13. The kit of claim 12, further comprises said second oligonucleotide.

14. The kit of claim 12, further comprises a labeled nucleotide triphosphate.

15. The kit of claim 12, further comprises a DNA polymerase suitable for said PCR reactions.

* * * * *